(12) United States Patent
Schultze et al.

(10) Patent No.: US 6,981,955 B2
(45) Date of Patent: Jan. 3, 2006

(54) SLEEVE-LIKE KNITTED STRUCTURE FOR USE AS A CASTLINER

(75) Inventors: Claudia Schultze, Greenville, DE (US); George W. Coulston, West Chester, PA (US)

(73) Assignee: Invista North America S.a.r.l., Wilmington, DE (US)

( * ) Notice: Subject to any disclaimer, the term of this patent is extended or adjusted under 35 U.S.C. 154(b) by 0 days.

(21) Appl. No.: 10/878,833

(22) Filed: Jun. 28, 2004

(65) Prior Publication Data

US 2005/0027219 A1 Feb. 3, 2005

Related U.S. Application Data

(60) Provisional application No. 60/484,445, filed on Jul. 2, 2003.

(51) Int. Cl.
*A61F 5/00* (2006.01)
(52) U.S. Cl. .............................. 602/3; 602/63; 602/61; 602/6
(58) Field of Classification Search .................... 602/3, 602/8, 60, 61, 62; 2/16, 22, 24
See application file for complete search history.

(56) References Cited

U.S. PATENT DOCUMENTS

| | | | | |
|---|---|---|---|---|
| 2,858,830 | A | * | 11/1958 | Robins ........................ 604/307 |
| 4,977,892 | A | * | 12/1990 | Ewall .......................... 602/52 |
| 5,016,622 | A | * | 5/1991 | Norvell ........................ 602/7 |
| 5,268,229 | A | * | 12/1993 | Phillips et al. .............. 428/400 |
| 5,474,522 | A | * | 12/1995 | Scholz et al. ................. 602/8 |
| 5,498,232 | A | * | 3/1996 | Scholz ......................... 602/8 |
| 5,512,354 | A | * | 4/1996 | Scholz et al. ................ 442/306 |
| 5,540,964 | A | | 7/1996 | Mallen |
| 5,540,982 | A | * | 7/1996 | Scholz et al. ................. 442/59 |
| 5,752,926 | A | * | 5/1998 | Larson et al. ................. 602/7 |
| 5,807,291 | A | * | 9/1998 | Larson et al. ................. 602/8 |
| 5,843,357 | A | * | 12/1998 | Seneker et al. ............. 264/204 |
| 5,882,322 | A | * | 3/1999 | Kim et al. .................... 602/6 |
| 5,948,707 | A | * | 9/1999 | Crawley et al. ............. 442/101 |
| 6,063,980 | A | * | 5/2000 | Peterson et al. ............. 602/49 |
| 6,540,706 | B1 | * | 4/2003 | Martin et al. ................. 602/6 |
| 6,667,351 | B2 | * | 12/2003 | Langohr et al. ............. 522/157 |
| 6,673,029 | B1 | * | 1/2004 | Watson ......................... 602/6 |
| 2003/0129904 | A1 | * | 7/2003 | Wolynes et al. ............. 442/211 |
| 2004/0006323 | A1 | * | 1/2004 | Hall et al. ................ 604/385.24 |
| 2004/0058072 | A1 | * | 3/2004 | Rearick et al. ............. 427/324 |
| 2004/0127881 | A1 | * | 7/2004 | Stevens et al. ........ 604/385.22 |
| 2004/0224587 | A1 | * | 11/2004 | Hayes et al. ................. 442/119 |
| 2005/0106971 | A1 | * | 5/2005 | Thomas ........................ 442/181 |

* cited by examiner

*Primary Examiner*—Henry Bennett
*Assistant Examiner*—Dinnatia Doster-Greene

(57) ABSTRACT

A castliner in the form of a three-dimensionally knitted sleeve comprises a microdenier yarn, and/or a spandex yarn, in particular, a spandex yarn having a flatter stress-strain curve than traditional spandex yarns. The use of the microdenier yarn contributes to the superior cushioning effect. The stretch and recovery properties of the particular spandex yarn contribute to superior fit and reduction of pressure points on the limb or body part to which the castliner is applied. Furthermore, the castliner is rendered water resistant and has significantly improved antimicrobial properties, both of which reduce incidents of skin irritation and unpleasant smell. As a result, the patient wearing the castliner of the invention is able to bathe and get wet without otherwise replacing the hard casting and castliner after such events.

10 Claims, 3 Drawing Sheets

100

100a

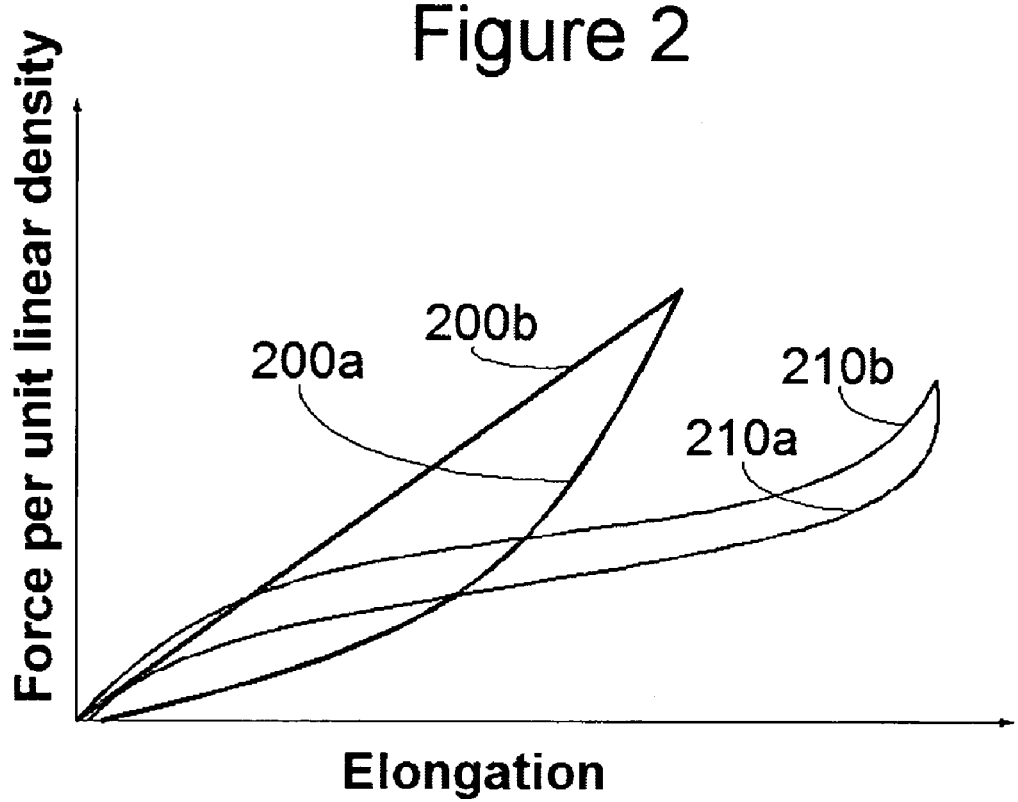

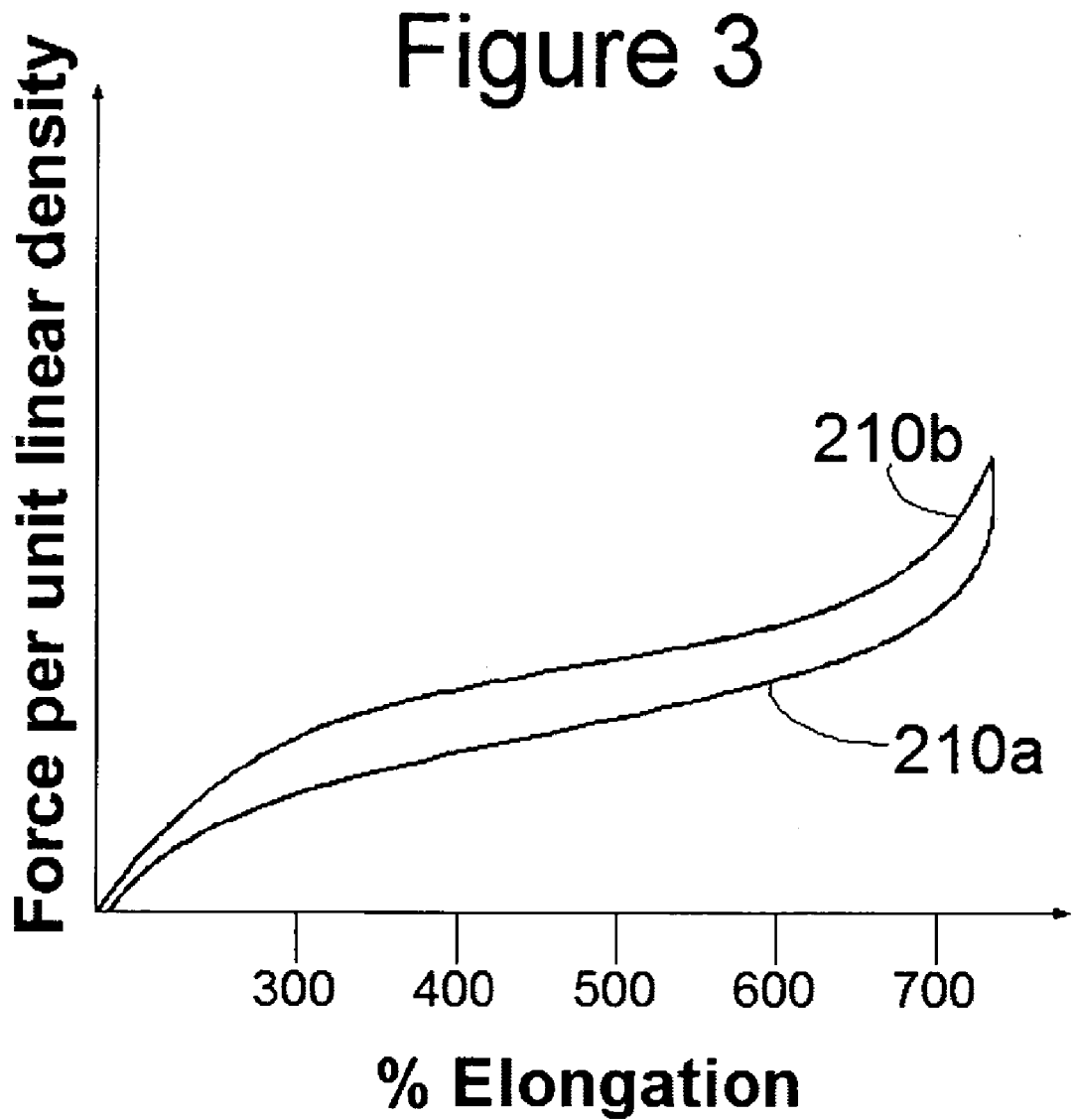

SLEEVE-LIKE KNITTED STRUCTURE FOR USE AS A CASTLINER

CROSS-REFERENCE TO RELATED APPLICATION

This application claims benefit of priority from Provisional Application No. 60/484,445 filed Jul. 2, 2003.

FIELD OF THE INVENTION

The present invention relates to a castliner, and particularly to a sleeve-like knitted structure, for use as a castliner having superior cushioning and enhanced comfortable conformance to the body, as well as exhibiting antimicrobial properties, decreased water uptake and an enhanced moisture transmission rate. More particularly the invention relates to a three-dimensional knitted sleeve adapted for use as a castliner and made from particular synthetic polymer fibers and knit in selected patterns.

BACKGROUND OF THE INVENTION

It is known to employ a cotton knit sock (e.g., single jersey knit) as a first layer and cotton or poly/cotton webbing for cushioning (also called padding) as a second layer under a hard shell casting material. Known casting materials are either of fiberglass or plaster-of-paris. In use, the known castliner comprises a cotton jersey sleeve, which is pulled over the limb being treated, and a cotton webbing wrapped around the limb. Typically, some skill is required for application of the castliner of this known type. Particular skill is needed during application of the layers of cotton webbing, which is cumbersome to apply. Especially important is the required thickness of cotton webbing which ultimately protects the limb during the cast removal process. A particular disadvantage of such known castliners is their poor water repellency and moisture transmission rate. Water retention by known castliners fosters the growth of bacteria causing patient complaints about: unpleasant odors, itching, and general discomfort.

An improvement to the foregoing known cotton cast lining is described in U.S. Pat. No. 5,540,964 to Mallen. Mallen discloses a cast lining which is capable of transporting moisture from beneath the cast to the air space within the cast and ultimately to the outside area. In one embodiment of the Mallen invention a fabric is formed from a blend of hydrophobic synthetic fibers (e.g., polyester) and a second fiber (spandex). This fabric is constructed into a tube with or without open ends and used as castliner beneath an orthopedic cast. Mallen's cast lining tube is then made "hydrophilic" according to methods disclosed therein. In general, the Mallen fabric conforms closely to the limb being treated due to the elastic fiber content of the tubular cast lining. Mallen specifically discloses use of LYCRA® (branded spandex from INVISTA S.à r.l. of Wilmington, Del.) in its construction.

Applicants have found various prior art cast lining materials disadvantageous in several modes of performance. First, jersey knit sleeve and cotton webbing can be difficult for unskilled casting room operators to apply uniformly. Second, the moisture absorption of these sleeve and webbing liners is high. Third, the sleeve and webbing lining can be stiff and can provide pressure points at joints especially. The Mallen (U.S. Pat. No. 5,540,964) cast lining is an improvement in conformance to the limb shape.

It would be desirable to improve cushioning and moisture transmission rate while minimizing the pressure points caused by elastic yarns in the construction. Typically, points of increased pressure on the limb are present in areas of the limb joints and where the limb changes diameter most abruptly.

Thus, a longstanding unmet need for a sleeve-like knitted castliner without the deficiencies of the prior art exists.

SUMMARY OF THE INVENTION

The present invention provides a castliner in the form of a three-dimensionally knitted tubing for use beneath an orthopedic cast with enhanced cushioning and comfortable conformance to the body. In addition, the sleeve-like knitted castliner of the present invention may provide enhanced moisture transmission rate, antimicrobial properties, and decreased water uptake. Moreover, the sleeve-like knitted castliner of the present invention may be easily and readily applied to limb or body portion in treatment by a relatively unskilled person.

The present invention provides a sleeve-like knitted castliner for use beneath an orthopedic cast, comprising a micro-denier yarn. The invention further includes a castliner comprising a spandex yarn having a specified stress/strain curve defining the elastic modulus of the spandex yarn. A preferred castliner comprises a spandex yarn in an amount of about 2 to about 20 percent by weight of the total castliner. A preferred castliner comprises LYCRA® 902C or LYCRA® 906 brand spandex fiber available from INVISTA S.à r.l. of Wichita, Kans. and Wilmington, Del. The sleeve-like knitted castliner of the invention provides enhanced cushioning as compared to castliners of the prior art, and conforms tightly to the limb or body portion under treatment.

Further in accordance with the present invention, there is provided a sleeve-like knitted castliner for use beneath an orthopedic cast, comprising an acrylic yarn treated with a phase change material. This castliner may also include a spandex yarn.

BRIEF DESCRIPTIONS OF THE DRAWINGS

FIG. 2 is a graph showing the stress-strain curves for conventional spandex yarn and for LYCRA® Soft brand spandex fiber, which is an alternative spandex yarn.

FIG. 3 is a graph showing a stress-strain curve for LYCRA® Soft brand spandex fiber.

DETAILED DESCRIPTION OF THE PREFERRED EMBODIMENTS

Figure 1:
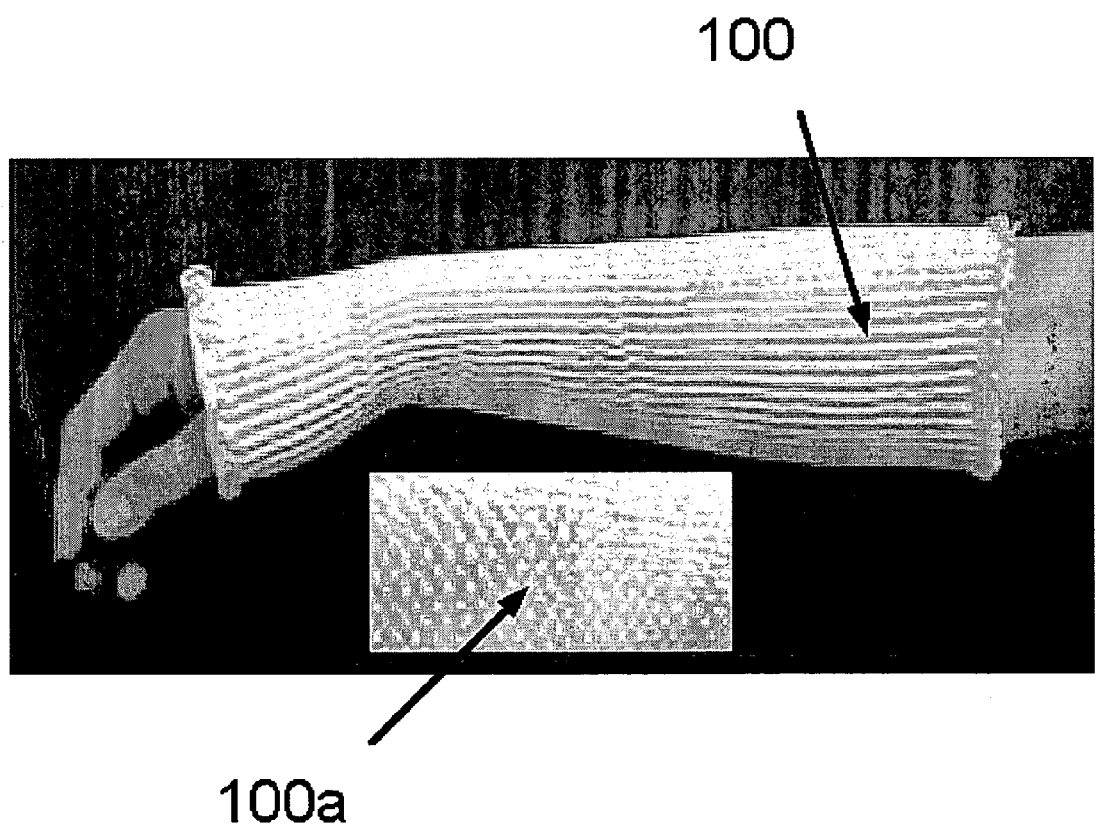
FIG. 1 is a photograph of the castliner of the present invention showing both the inside and the outside of its knitted tubular structure.

The invention provides a castliner for use beneath an orthopedic cast. Such a castliner is shown generally at 100 in FIG. 1. The castliner comprises a microdenier yarn. The term microdenier means having a single filament denier of less than one, or a decitex (dtex) of 1.1 or less. The use of a microdenier yarn provides superior cushioning and comfort as compared to yarns of the prior art. The microdenier yarn may be polyester or nylon. Alternatively, the microdenier yarn may be acrylic. Suitable polyester microfiber yarns are those with yarn counts such as 55 dtex and 100 filaments and 78 dtex and 100 filaments known as MICROMATTIQUE® (Type 935T from INVISTA S.à r.l., Wilmington, Del.) and used typically as a 2 ply yarn in a preferred construction. The castliner may be in the form of a three-dimensional knitted tubing. By "three-dimensional" is meant that the castliner has some degree of depth to it, due to the cushioning characteristics imparted by the microdenier yarn.

Further in accordance with the present invention, the castliner of the present invention may additionally comprise a spandex yarn, elastane yarn or polyester bicomponent yarns known as ELASTERELL-P™ from INVISTA™ of Wilmington, Del. The terms spandex and elastane are used interchangeably in the art. The spandex yarn is knitted with the microdenier yarn. An example of a branded spandex yarn suitable for use with the present invention is LYCRA®, sold by of INVISTA™ of Wilmington, Del. Such spandex yarns will be referred to hereinafter as traditional spandex yarns. Traditional spandex yarns such as LYCRA® have a dtex of about 10 to about 500.

The castliner of the present invention may alternatively comprise a spandex yarn which is made from a filament characterized by a flatter stress/strain curve than the filament of the spandex yarn described in the previous paragraph. Such yarns will be referred to hereinafter as alternative spandex yarns. Examples of such alternative spandex yarns suitable for use with the present invention are LYCRA® 902C and LYCRA® 906, also sold by INVISTA™. LYCRA® 902C and LYCRA® 906 are copolyether based spandex with a combination of high elongation and flat stress-strain behavior and the low hysteresis in comparison with other commercially available spandex filaments with LYCRA® high unload power.

To illustrate the difference between traditional LYCRA® yarns and LYCRA® 902C, reference is made to FIG. 2. FIG. 2 is graph of the stress-strain curves for a traditional spandex filament, and for LYCRA® 902C. Conventional LYCRA® filaments may have a stress-strain curve represented by 200a and 200b. LYCRA® 902C has a stress-strain curve represented by 210a and 210b. The latter stress-strain curve, 210a and 210b, is flatter than the stress-strain curve 200a and 200b. This distinction is based on the relative slope of the corresponding curves labeled 200a and 210a vs. curves 200b and 210b. For LYCRA® Soft brand spandex, the load and unload portions of the stress-strain curve can be substantially parallel within an elongation range of from about 300% to about 500%. The stress or force acting on the spandex filament, straining the filament, follows two different paths: path 200a (or 210a) while elongating and path 200b (or 210b) while retracting. This difference in path "a" and path "b" is known in the art as the hysteresis of the stress-strain curve. As a result of this low hysteresis in the stress-strain curve of the yarn of the present invention, pressure on the castliner treated limb is reduced for those points where the castliner is more greatly stretched versus traditional spandex yarns. The modulus of elasticity is the initial slope of the stress-strain curve.

It should be noted that a castliner made from alternative spandex yarns will also have a unique stress/strain curve which may be distinct from the stress/strain curve of the filament. In any case, the stress/strain curve as described above quantifies the stretch and recovery properties. Regardless of whether traditional or alternative spandex yarns are used, the use of spandex yarns provides stretch and recovery properties to the cast liner. The spandex yarn, either traditional or alternative, typically comprises about 2 to about 20 percent by weight of the castliner. The spandex yarns used with the present invention, either traditional or alternative, may have covering filaments, such as nylon.

In one alternative embodiment of the present invention, the spandex yarn may be knitted with an acrylic yarn, instead of a nylon or polyester yarn. In this embodiment, the acrylic yarn may contain a phase-change material. Such a material is a mixture of different chain-length hydrocarbons, and is commercially available from OUTLAST®, 6235 Lookout Road, Boulder, Colo. 80301, USA. The use of a phase change material (PCM) helps to reduce temperature spikes for the user, and to reduce sweat, thus making a castliner of the present invention more comfortable for the wearer.

The castliner of the present invention may be constructed in the form of a circular knitted tubing using a seamless knitting machine. A suitable machine is the Santoni, SM8-8TOP, commercially available from Santoni of Italy. The seamless circular knitting machine is set to operate with 10 needles in the up position and 10 needles in the down position for the typical constructions used herein; but many variations know to the skilled practitioner of circular knitting are possible. In cases where the castliner knit tubing is being adapted for a finger castliner or for a full-body castliner, the numbers of needles used in either up or down positions is varied between about 2 to about 20. Patterns selected for the knit construction include a chess board, ribbed, doubled ribbed, or diamond patterns. In general, these patterns are three-dimensional knit structures. The inset of FIG. 1 illustrates a checkerboard pattern at 100a. In a preferred embodiment, a circular knitted tubing may be knitted into a checkerboard pattern from polyester yarns of 1.1 decitex (dtex) and less and from LYCRA® yarns, having covering filaments of nylon typically, the LYCRA® having a dtex of about 10 to about 500.

In order to achieve very low levels of water uptake in the castliner rendering the castliner material hydrophobic, it may be advantageous to provide a fluorochemical surface treatment to the castliner. This treatment may provide the castliner with a water uptake of less than 200 percent, generally less 150 percent. A suitable fluorochemical treatment is provided by a TEFLON® fluoropolymer resin finish (known as ZONYL® 555 and available from E. I. DuPont.de Nemours and Company, Inc., Wilmington, Del., USA) applied to the yarns comprising the knitted tubing. A treatment with ZONYL® 555 padded onto the castliner material in an amount from about 2.5% to 7.5% by weight was found to be effective. The use of the fluorochemical surface treatment also improves drying time. Typically, the drying time of the cast liner of the present invention, measured in open air, is less than five hours. In addition, the use of the fluorochemical surface treatment also minimizes water contact with the patient. This measured by water contact angle, which, with the present invention, is greater than 140 degrees. This minimized water contact is also measured by water repellency. The castliner of the present invention is characterized by a water repellency rating of about 6 and greater.

The castliner of the present invention may also include an antimicrobial agent. Such agent may be included in the yarn. Examples of yarns containing silver as an antimicrobial agent include a sheath-core yarn having silver particles in the sheath, FossFiber® with AgION™ commercially available from Foss Manufacturing Company, Inc., Hampton, N.H., Xstatic® yarn, available from SAUQUOIT Industries, Inc., Scranton, Pa., USA having silver deposited on the yarn, or A.M.Y.™ yarn, commercially available from UNIFI Inc., Greensboro, N.C., USA, having silver spun into the yarn polymer. Alternatively, a topical finish may be used on the castliner. In any case, the castliner of the present invention is characterized by a reduction in the growth rate of bacteria by at least $\log_{10}(2)$ based on test methods know as ASTM E2149-01 "Standard Test Method for Determining the Antimicrobial Activity of Immobilized Antimicrobial Agents Under Dynamic Contact Conditions" and MTCC Test Method 100-1999 "Assessment of Antibacterial Finishes on Textile Materials."

The knitted construction and the materials of the castliner of the present invention may provide improved moisture vapor transmission. A castliner of the present invention may be characterized by a moisture vapor transmission rate of at least 800 grams per square meter per day, measured when the castliner is stretched. This moisture vapor transmission rate can enhance the antimicrobial properties of the castliner as described above.

The castliner of the present invention, constructed as described above, provides superior cushioning, comfort and simple application. In particular, the use of a microdenier yarn may contribute to the cushioning effect. The stretch and recovery properties of the spandex yarn of the castliner may contribute to provide a castliner having superior fit and reduction of pressure points on the limb or body part to which the castliner is applied. Furthermore, the castliner may be rendered water resistant and significantly improved in antimicrobial properties which reduce incidents of skin irritation and unpleasant smell. As a result, the patient wearing the castliner of the invention is able to bathe and get wet without otherwise replacing the hard casting and castliner after such events.

The invention will be described in greater detail with reference to the following examples which are intended to illustrate the invention without restricting the scope thereof.

TEST METHODS

Water (Moisture) Uptake Test Method

In this test method a circular sample 2 inches (51 mm) in diameter was cut. This circular sample was weighed (initial dry weight). Each sample was submerged in cool water for 30 seconds, force was applied to keep the sample submerged. By hand the sample was squeezed to force as much water from it as possible. The squeeze dry sample was weighed again (final wet weight). The average of three trials were taken. In the case of fluorochemical treated samples the hand squeeze procedure was omitted as these could be shaken to remove excess water. The difference between the initial weight and the wet weight expressed as a percentage increase in weight was called the moisture pickup.

Water Repellency Rating (DuPont Water Drop Test)

This test determines a finished fabric's resistance to wetting by aqueous liquids. Drops of water-alcohol mixtures of varying surface tensions are placed on the fabric, and the extent of surface wetting is determined visually. This test provides a rough index of aqueous stain resistance. Generally, the higher the water repellency rating, the better the finished fabric's resistance to staining by water-based substances.

In this test, a fabric was placed face up on white blotting paper on a flat horizontal surface. Beginning with Test Liquid No. 1, which was a mixture of 2% isopropyl alcohol and 98% distilled water, drops were placed approximately 5 mm in diameter or 0.05 ml in volume on the test fabric in three locations. The drops were observed for 10 seconds from an approximate 45° angle. If at least two of the three drops do not penetrate or wet the fabric and do not show wicking around the drops, the drops of test Liquid No. 2, which was a mixture of 5% isopropyl alcohol and 95% distilled water, were placed on an adjacent site, and the step of placing the drops on the test fabric in three locations was repeated. The steps of observing the drops, and adding drops of test Liquid No. 2 were repeated, until at least two of the three drops had wet or showed wicking into the fabric within 10 seconds. The steps of observing the drops and adding drops were repeated for test Liquid No. 3, which was a mixture of 10% isopropyl alcohol and 90% distilled water, for test Liquid No. 4, which was a mixture of 20% isopropyl alcohol and 80% distilled water, for test Liquid No. 5, which was a mixture of 30% isopropyl alcohol and 70% distilled water, and for test Liquid No. 6, which was a mixture of 40% isopropyl alcohol and 60% distilled water. The fabric's water repellency rating was the highest numbered liquid for which at least two of the three drops did not wet or wick into the fabric.

Drying Time Measured in Open Air

In this test method a circular sample 2 inches (51 mm) in diameter was cut. This circular sample was weighed (initial dry weight). Each sample was submerged in cool water for 30 seconds, force was applied to keep the sample submerged exactly as had been done for the moisture pickup test method. While holding each sample with forceps the sample was shaken 3 times to expel excess water. After shaking the wet samples were weighed and then placed on a plastic sheet and allowed to air dry. The weight of each sample was recorded once per hour for a total of 3 hours. The difference in weight between the initial weight and weight after each hour of the test was the water loss per hour. This weight loss was expressed in grams of water evaporated from the samples and as a percentage loss in weight due to evaporation.

Water Contact Angle

The water contact angle method used was along the lines of ASTM D724-99 Standard Test Method for Surface Wettability of Paper (Angle-of-Contact Method). Using a microscope and angle measuring comparators the contact angle was estimated visually. The measurement was repeated with a soap solution of the MTCC standard detergent 124 powder made up to 2 weight % in distilled water at 38° C. for those cases where the contact angle was quite high.

Moisture Vapor Transmission Rate (MVTR)

Moisture vapor transmission rate, or MVTR, is determined according to ASTM Standard E96-66, Procedure BW (Inverted Water Method at 23 C). Standard E96-66 permits determination of the rate of water vapor transmission of materials in sheet form. Procedure BW is for use when materials to be tested may in service be wetted on one surface but under conditions where the hydraulic head is relatively unimportant and moisture is governed by capillary and water vapor diffusion forces. ASTM Standard E96-66 provides further details of how to perform the measurements.

Salzmann Medico Sub-bandage Pressure Monitor MST Mark 3 (Salzmann Group, St. Gallen, Switzerland) was used to evaluate pressure points as the castliner sleeve was fitted to the limb under treatment. In all cases a Size 4 mannequin leg form was used in testing. Pressure points could be measured in 6 separate areas of the leg, denoted as b, b1, c, d, f, and g. In not all cases did the castliner sleeve cover the entire mannequin leg form, as a result, fewer than 6 separate measurements may have been taken. Pressure is reported from the Salzmann MST Mark 3 in units of mm of mercury (mmHg).

Fabric Stretch and Recovery

Fabric stretch and recovery for a stretch woven fabric is determined using a universal electromechanical test and data acquisition system to perform a constant rate of extension tensile test. A suitable electromechanical test and data acquisition system is available from Instron Corp, 100 Royall Street, Canton, Mass., 02021 USA. Two fabric properties are measured using this instrument: fabric stretch and the fabric growth (deformation). The available fabric stretch is the amount of elongation caused by a specific load between 0 and 30 Newtons and expressed as a percentage change in length of the original fabric specimen as it is stretched at a rate of 300 mm per minute. The fabric growth is the unrecovered length of a fabric specimen which has been held at 80% of available fabric stretch for 30 minutes then allowed to relax for 60 minutes. Where 80% of available fabric stretch is greater than 35% of the fabric elongation, this test is limited to 35% elongation. The fabric growth is then expressed as a percentage of the original length. The elongation or maximum stretch of stretch woven fabrics in the stretch direction is determined using a three-cycle test procedure. The maximum elongation measured is the ratio of the maximum extension of the test specimen to the initial sample length found in the third test cycle at load of 30 Newtons. This third cycle value corresponds to hand elongation of the fabric specimen.

Antimicrobial Activity

The antimicrobial activity of the castliner of was measured using several test methods, these were: ASTM E2149-01 "Standard Test Method for Determining the Antimicrobial Activity of Immobilized Antimicrobial Agents Under Dynamic Contact Conditions" and AATCC Test Method 100-1999 "Assessment of Antibacterial Finishes on Textile Materials" and the "Shake-Flask Test" with test # Dow 923, known in the art as the Shake-Flask test. All of these testing procedures were made available as a service from NAMSA, 6750 Wales Road, Northwood, Ohio 43619, USA with an ISO 10993 certificate of compliance.

EXAMPLES

Example 1

Part a—A second castliner sample of the invention was constructed from a double ply of 70 denier 100 filament COOLMAX® polyester yarn (INVISTA™ North America Inc.) and 8% by weight of 70 denier LYCRA® brand spandex single covered with 20 denier 7 filament nylon.

Part b—A first castliner sample of the invention was constructed from a double ply of 70 denier 100 filament COOLMAX® polyester yarn (INVISTA™ North America Inc. and 8% by weight of 20 denier LYCRA® brand spandex single covered with 20 denier 7 filament nylon.

Part c—A third castliner sample of the invention was constructed from a double ply of 70 denier 100 filament COOLMAX® polyester yarn (INVISTA™ North America Inc.) and 8% by weight of 40 denier LYCRA® brand spandex single covered with 20 denier 7 filament nylon.

The three samples (a, b and c) were tested using the moisture uptake test method using a circular sample 2 inches (51 mm) in diameter cut from each tubing. Each of the samples (a, b and c) was also separately treated with a fluorochemical finish, ZONYL® 555 by a padding method. The 3 samples untreated with fluorochemical finish were controls for the 3 treated samples. The following table summarizes these results for moisture uptake by the materials of the castliner.

| Sample | ZONYL® 555 (% by weight) | initial weight in grams | squeezed weight ave. | % moisture pickup |
|---|---|---|---|---|
| a | 0 | 1.628 | 5.379 | 330.41 |
| b | 0 | 1.026 | 3.468 | 338.01 |
| c | 0 | 1.380 | 4.510 | 326.79 |
| a | 2.5 | 1.8 | 2.947 | 163.70 |
| b | 5.0 | 1.466 | 1.909 | 130.20 |
| c | 7.5 | 1.568 | 1.911 | 121.88 |

These data show that the fluorochemical (ZONYL® 555) treated samples all performed with a moisture pickup of less than half that moisture pickup of the untreated samples. A castliner tubing of fluorochemical treated material would be expected to be highly moisture resistant.

In order to estimate the amount of fluorochemical applied to the castliner, the treated samples were analyzed for total fluoride ion by ion chromatography (IC) using the standard methods know to practitioners in the art.

These results for the ZONYL® treated materials are given in the following table.

| Sample | ZONYL® 555 (% by weight) | Total Fluorine as fluoride ion (parts per million) |
|---|---|---|
| a | 2.5 | 1375 |
| b | 5.0 | 2010 |

All of the fluorochemical treated samples were measure for their contact angle with a water droplet (along the lines of the ASTM D724-99 method). In all samples a, b, and c the contact angle was not measurable with distilled water. The measurements were repeated with soap solution (AATCC standard detergent 124 powder; 2 weight % in distilled water). In all samples a, b, and c the soap solution contact angle was greater than 140 degrees of arc. Evidently, the very high surface energy imparted by the fluorochemical treatment to the castliner materials of construction prevented and substantial water wetting.

Drying time measured in open air: In this test method a circular sample 2 inches (51 mm) in diameter was cut. This circular sample was weighed (initial dry).

The three samples (a, b and c) were tested using the test method for drying time measured in open air. Identically to the moisture uptake method a circular sample 2 inches (51 mm) in diameter cut from each tubing. Each of the samples (a, b and c) was also separately treated with a fluorochemical finish, ZONYL® 555 by a padding method. The 3 samples untreated with fluorochemical finish were controls for the 3 treated samples. The following table summarizes these results for drying time measured in open air by the materials of the castliner tubing. These data show again that very little moisture is acquired by the fluorochemical treated castliner material and that these treated samples air dry at a substantially constant rate over the 3 hour measurement period.

| Sample | ZONYL ® 555 (% by weight) | % water uptake (measured after shaking) | % water loss after 1 hour | % water loss after 2 hours | % water loss after 3 hours |
|---|---|---|---|---|---|
| a | 0 | 441.7 | 34.8 | 22.9 | 29.7 |
| b | 0 | 672.7 | 51.2 | 33.7 | 44.6 |
| c | 0 | 315.7 | 33.3 | 23.2 | 28 |
| a | 2.5 | 256.8 | 25.9 | 19.9 | 21.9 |
| b | 5.0 | 114. | 30.8 | 20.4 | 23.1 |
| c | 7.5 | 7.5 | 9.6 | 0.0 | 0.0 |

These three samples were tested for interface pressure points using Salzmann Medico MST Mark 3 tester and a Size 4 mannequin leg form. Six potential leg pressure points could be measured, denoted as points b, b1, c, d, f, and g in the Salzmann Medico MST MKIII measurement protocol. Pressure points b and b1 corresponded to ankle and subcalf portions of the leg, c and d corresponded to calf and knee portions, while measurements f and g corresponded to the largest diameter portions of the thigh.

Salzmann Medico MST MKIII Measurement Summary

| Measurement point (Size 4 leg) | Sample a pressure (mmHg) | Sample b pressure (mmHg) | Sample c Pressure (mmHg) |
|---|---|---|---|
| b | 17 | 11 | 13 |
| b1 | 16 | 11 | 13 |
| c | 17 | 11 | 12 |
| d | 15 | 10 | 12 |
| f | 15 | 10 | 9 |
| g | 10 | 5 | — |

Moisture Vapor Transmission (MVT) rate was measured for sample a; in three states of stretch: relaxed, partial stretch and full stretch. The results are summarized in the following table showing a more stretched fabric transmits greater amounts of moisture.

| Sample a (70 denier LYCRA ® in the construction) | weight in grams | weight in grams after 24 hours | Transmission rate (grams per 24 hours per square meter) |
|---|---|---|---|
| a (relaxed) | 217.58 | 214.83 | 869 |
| a (partially stretched) | 222.87 | 217.89 | 1573.68 |
| a (fully) stretched) | 221.56 | 215.37 | 1956.04 |

Example 2

In Part 1 of this example a castliner sample of the invention was constructed from a double ply of 70 denier 100 filament COOLMAX® polyester yarn (INVISTA™ North America Inc.) and 70 denier LYCRA® brand spandex single covered with 20 denier 7 filament nylon and then knitted and scoured; variations on this construction are noted in the following table. Those samples containing silver ion and a single sample treated with TINOSAN® antimicrobial (from Ciba Specialty Chemicals, Ardsley, N.Y., USA, 10502-2699) showed activity against the organisms tested: S. Aureus and Kleb. Pneumoniae. In Part 2 of this example a castliner sample of the invention was constructed from the materials noted in the table. Only the silver containing castliner was effective against any microbe tested. Apparently, the ZONYL® 555 TEFLON® treatment interferes with the antimicrobial action of the silver ion. However, this observation was not conclusive.

| Sample | Anti-microbial agent | Test method | % Reduction of activity (*Staph. Aureus*) | % Reduction of activity (*Kleb. Pneumon.*) | $Log_{10}$ kill rate | comment |
|---|---|---|---|---|---|---|
| Example 2, Part 1. | | | | | | |
| FossFiber ™ | Includes 15% staple fibers | ASTM E2149 | 88.46 | | <1 | |
| Xstatic ® | Includes Silver coated nylon yarn in each 4th feed | ASTM E2149 | 99.96 | | 3.397 | |
| Untreated control | | ASTM E2149 | — | | | No reduction |
| treated | TINOSAN ® anti-microbial from Ciba Specialty Chemicals | AATCC100 | 54.4 | 97.93 | <1 | |

-continued

| Sample | Anti-microbial agent | Test method | % Reduction of activity (*Staph. Aureus*) | % Reduction of activity (*Kieb. Pneumon.*) | Log₁₀ kill rate | comment |
|---|---|---|---|---|---|---|
| Example 2, Part 2. | | | | | | |
| FossFiber ™ and Zonyl ® 555 | 48% FossFiber ™ 48% TACTEL ® nylon, 4% LYCRA ® | ASTM E2149 | — | | | No reduction |
| FossFiber ™ | 48% FossFiber ™ 48% TACTEL ® nylon, 4% LYCRA ® | ASTM E2149 | 55. | | <1 | |
| Untreated control | 48% TACTEL ® nylon, 24% cotton, 24% COOLMAX ® 4% LYCRA ® | ASTM E2149 | — | | | No reduction |
| Untreated control | 96% TACTEL ® nylon, 4% LYCRA ® | ASTM E2149 | — | | | No reduction |

What is claimed is:

1. A castliner for use beneath an orthopedic cast, comprising a microdenier polyester yarn and further comprising a covered spandex yarn in an amount of about 2 to about 20 percent by weight of the castliner and wherein the spandex yarn has a load and unload portion of the stress-strain curve substantially parallel within an elongation range of from about 300% to about 500%.

2. The castliner of claim 1, characterized by a moisture vapor transmission rate of at least 800 grams per square meter per day; measured when the castliner is unstretched.

3. The castliner of claim 1, further comprising a fluorochemical treatment on the surface of the castliner.

4. The castliner of claim 3, wherein the castliner is characterized by a water uptake of less than 200 percent.

5. The castliner of claim 3, characterized by a drying time measured in open air of less than 5 hours.

6. The castliner of claim 3, characterized by a water contact angle greater than 140 degrees.

7. The castliner of claim 3, characterized by a water repellency rating of about 6 and greater.

8. The castliner of claim 1, characterized by an antimicrobial property characterized by a reduction in the growth rate of bacteria by at least $\log_{10}(2)$.

9. The castliner of claim 1, wherein the spandex yarn and the microdenier yarn are knitted together in a pattern selected from the group consisting of checkerboard, ribbed, double ribbed, and diamond.

10. A castliner in the form of a three-dimensionally knitted tubing for use beneath an orthopedic cast, comprising an acrylic yarn treated with a phase change material and further comprising covered spandex yarn knitted with the acrylic yarn and wherein the spandex yarn has a load and unload portion of the stress-strain curve substantially parallel within an elongation range of from about 300% to about 500%.

* * * * *